United States Patent
Gil et al.

(10) Patent No.: US 9,050,138 B2
(45) Date of Patent: Jun. 9, 2015

(54) VERTEBRAL ROD CONNECTOR AND METHODS OF USE

(75) Inventors: Carlos E. Gil, Collierville, TN (US); Jason Michael May, Cordova, TN (US); Aleksandr G. Zolotov, Collierville, TN (US); Joshua W. Simpson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1078 days.

(21) Appl. No.: 12/695,563

(22) Filed: Jan. 28, 2010

(65) Prior Publication Data

US 2011/0184462 A1    Jul. 28, 2011

(51) Int. Cl.
*A61B 17/70*    (2006.01)

(52) U.S. Cl.
CPC .......... *A61B 17/7001* (2013.01); *A61B 17/7032* (2013.01)

(58) Field of Classification Search
CPC ........... A61B 17/7032; A61B 17/7034; A61B 17/7041; A61B 17/7025; Y10T 403/7105; Y10T 403/7129; Y10T 403/7141; Y10T 403/7194; F16B 7/044
USPC .................................................. 606/264–278
See application file for complete search history.

(56) References Cited

U.S. PATENT DOCUMENTS

| | | | |
|---|---|---|---|
| 923,071 A * | 5/1909 | Palmer | 439/782 |
| 5,437,208 A * | 8/1995 | Cheng | 74/551.1 |
| 5,480,401 A | 1/1996 | Navas | |
| 5,586,984 A | 12/1996 | Errico et al. | |
| 5,615,965 A | 4/1997 | Saurat et al. | |
| 5,643,260 A * | 7/1997 | Doherty | 606/270 |
| 5,647,873 A | 7/1997 | Errico et al. | |
| 5,938,663 A | 8/1999 | Petreto | |
| 5,947,967 A * | 9/1999 | Barker | 606/278 |
| 5,961,516 A | 10/1999 | Graf | |
| 5,984,924 A * | 11/1999 | Asher et al. | 606/264 |
| 6,482,207 B1 * | 11/2002 | Errico | 606/264 |
| 6,595,992 B1 | 7/2003 | Wagner et al. | |
| 6,610,062 B2 | 8/2003 | Bailey et al. | |
| 6,770,075 B2 | 8/2004 | Howland | |
| 6,802,844 B2 | 10/2004 | Ferree | |
| 6,991,632 B2 | 1/2006 | Ritland | |
| 7,090,674 B2 | 8/2006 | Doubler et al. | |
| 7,207,992 B2 | 4/2007 | Ritland | |
| 7,211,087 B2 | 5/2007 | Young | |
| 7,241,074 B2 | 7/2007 | Thomke et al. | |
| 7,335,201 B2 | 2/2008 | Doubler et al. | |
| 7,338,491 B2 | 3/2008 | Baker et al. | |
| 7,572,278 B2 | 8/2009 | Suzuki et al. | |
| 7,704,271 B2 | 4/2010 | Abdou | |
| 7,819,902 B2 * | 10/2010 | Abdelgany et al. | 606/267 |
| 7,862,593 B2 * | 1/2011 | Clement et al. | 606/260 |
| 8,048,125 B2 * | 11/2011 | Mitchell et al. | 606/264 |
| 2003/0171751 A1 | 9/2003 | Ritland | |
| 2005/0177164 A1 | 8/2005 | Walters et al. | |
| 2008/0177166 A1 | 7/2008 | Pronovost et al. | |
| 2008/0300633 A1 | 12/2008 | Jackson | |

\* cited by examiner

*Primary Examiner* — Mary Hoffman

(57) ABSTRACT

A vertebral rod connector includes a first portion configured to engage a fastener construct and define a first longitudinal axis. A second portion is configured to engage a vertebral rod and define a second longitudinal axis disposed transverse to the first longitudinal axis. A flexible linking portion is disposed for connecting the first portion with the second portion. The linking portion has a bifurcated configuration oriented transverse to the first longitudinal axis. Methods of use are disclosed.

16 Claims, 3 Drawing Sheets

VERTEBRAL ROD CONNECTOR AND METHODS OF USE

TECHNICAL FIELD

The present disclosure generally relates to medical devices for the treatment of spinal disorders, and more particularly to a vertebral rod system including a flexible connector disposed between a spinal construct and a vertebral fastener in a configuration that facilitates multi-axial movement of the spinal construct relative to the vertebral fastener.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders include discectomy, laminectomy, fusion and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods may be attached via fasteners to the exterior of two or more vertebral members. This disclosure describes an improvement over these prior art technologies.

SUMMARY

Accordingly, a vertebral rod system is provided, which includes a flexible connector disposed between a spinal construct and a vertebral fastener in a configuration that facilitates multi-axial movement of the spinal construct relative to the vertebral fastener.

In one particular embodiment, in accordance with the principles of the present disclosure, a vertebral rod connector is provided. The vertebral rod connector includes a first portion configured to engage a fastener construct and define a first longitudinal axis. A second portion is configured to engage a vertebral rod and define a second longitudinal axis disposed transverse to the first longitudinal axis. A flexible linking portion is disposed for connecting the first portion with the second portion. The linking portion has a bifurcated configuration oriented transverse to the first longitudinal axis.

In an alternate embodiment, a vertebral rod bracket is provided. The vertebral rod bracket includes an elongated collar defining a cavity configured to receive a fastener construct and defining a longitudinal axis. A flexible bifurcated extension is disposed in a transverse orientation relative to the longitudinal axis. The flexible bifurcated extension includes a first member extending from the elongated collar and a second member. A flange extends from the second member and defines one opening orientated transverse to the longitudinal axis. The opening is configured to slidably receive a vertebral rod.

In another alternate embodiment, a vertebral rod system is provided. The vertebral rod system includes a pedicle screw assembly, and a bracket. The bracket includes an elongated collar defining a cavity configured to receive the pedicle screw assembly and defining a longitudinal axis. A flexible bifurcated extension is disposed in a transverse orientation relative to the longitudinal axis and includes a first member extending from the elongated collar and a second member. A flange extends from the second member and defines one opening orientated transverse to the longitudinal axis. The opening is configured to slidably receive a vertebral rod.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
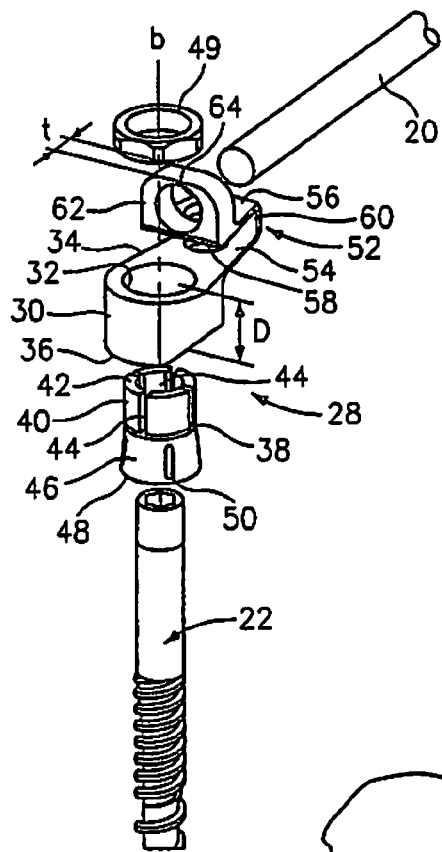
FIG. 1 is a perspective view of one particular embodiment of a vertebral rod system in accordance with the principles of the present disclosure.

The exemplary embodiments of the vertebral rod system and methods of use disclosed are discussed in terms of medical devices for the treatment of spinal disorders and more particularly, in terms of a vertebral rod system including a flexible connector disposed between a spinal construct and a vertebral fastener in a configuration that facilitates multi-axial movement of the spinal construct relative to a vertebral fastener. It is envisioned that the vertebral rod system and methods of use disclosed provide stability and maintains structural integrity while reducing stress on spinal elements. It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is further envisioned that the present disclosure may be employed with surgical treatments including open surgery and minimally invasive procedures, of such disorders, such as, for example, discectomy, laminectomy, fusion, bone graft and implantable prosthetics. It is contemplated that the present disclosure may be employed with other osteal and bone related applications, including those associated with diagnostics and therapeutics. It is further contemplated that the disclosed vertebral rod system may be employed in a surgical treatment with a patient in a prone or supine position, employing a posterior, lateral or anterior approach. The present disclosure may be employed with procedures for treating the lumbar, cervical, thoracic and pelvic regions of a spinal column. The system and methods of the present disclosure may also be used on animals, bone models and other non-living substrates, such as for training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The following discussion includes a description of a vertebral rod system, related components and exemplary methods of employing the vertebral rod system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there is illustrated components of a vertebral rod system in accordance with the principles of the present disclosure.

The components of the vertebral rod system are fabricated from materials suitable for medical applications, including metals, polymers, ceramics, biocompatible materials and/or their composites, depending on the particular application and/or preference of a medical practitioner. For example, the components of the vertebral rod system, individually or collectively, can be fabricated from materials such as commercially pure titanium, titanium alloys, cobalt-chrome alloys, thermoplastics such as polyaryletherketone (PAEK) including polyetheretherketone (PEEK), polyetherketoneketone (PEKK) and polyetherketone (PEK), carbon-PEEK composites, carbon fiber PEEK, PEEK-BaSO$_4$ polymeric rubbers, biocompatible materials such as polymers including plastics, metals, ceramics and composites thereof, rigid polymers including polyphenylene, polyamide, polyimide, polyetherimide, polyethylene, epoxy, and different components of the vertebral rod system may have alternative material composites to achieve various desired characteristics such as strength, rigidity, elasticity, compliance, biomechanical performance, durability and radiolucency or imaging preference.

The vertebral rod system is configured for attachment to vertebrae during surgical treatment of a spinal disorder, examples of which are discussed herein. The vertebral rod system has a construct, such as, for example, a vertebral rod 20 and a fastener construct such as, for example, a pedicle screw assembly 22 that attaches the vertebral rod system to bony tissue, as will be discussed. Vertebral rod 20 includes an upper section 24, a lower section 26 and defines a longitudinal axis a.

The vertebral rod system includes a vertebral rod connector such as, for example, vertebral rod bracket 28. Vertebral rod bracket 28 includes a first portion such as, for example, an elongated collar 30 that is configured to engage pedicle screw assembly 22. Collar 30 defines a cavity 32 configured to receive pedicle screw assembly 22 for support thereof. Collar 30 extends from a first end 34 to a second end 36 and defines a longitudinal axis b. Collar 30 has a cylindrical cross section and cavity 32 is elongated along axis b such that cavity 32 can support components of the vertebral rod system. It is contemplated that collar 30 may have alternative cross section configurations such as rectangular, polygonal and oval. Collar 30 has a depth D. It is envisioned that depth D may be in a range of approximately 2-12 millimeters (mm).

An insert 38 has a first section 40 configured for disposal within cavity 32. First section 40 has a cylindrical configuration that defines a wall 42. Wall 42 includes a plurality of equidistantly spaced apart openings 44, which provide flexibility to wall 42. A locking nut 49 is threaded with an outer surface of wall 42 to fix insert 38 with collar 30, and pedicle screw assembly 22 with bracket 28. Upon fixation of locking nut 49 with insert 38, the flexibility of wall 42 facilitates press-fit engagement of insert 38 with pedicle screw assembly 22. Wall 42 defines a portion of a cavity 44 configured to receive pedicle screw assembly 22.

Insert 38 has a second section 46 configured to receive pedicle screw assembly 22. Second section 46 has a cylindrical configuration that defines a wall 48. Wall 48 includes a plurality of equidistantly spaced apart openings 50, which provide flexibility to wall 48. Wall 48 is flared outwardly and defines a portion of cavity 44. The flared configuration and openings 50 facilitate press-fit engagement of insert 38 within cavity 32. It is contemplated that openings 44, 50 may be non-uniformly disposed about insert 38, and/or insert 38 may include one or a plurality of openings 44, 50.

A flexible linking portion such as, for example, a bifurcated extension 52 is disposed in a transverse orientation relative to axis b. Extension 52 includes a first member 54 and a second member 56 disposed in substantially parallel alignment. First member 54 extends from first end 34 and defines an elongated opening 58, which enhances flexibility of extension 52. It is envisioned that first member 54 may not include an opening. It is further envisioned that first member 54 may include one or a plurality of openings.

First member 54 is connected with second member 56 via an arcuate web 60. Web 60 is a flexible joining portion disposed between members 54, 56 and has a continuous surface extending therebetween. It is contemplated that web 60 may have a hinge configuration. It is further contemplated that web 60 may have various geometric configurations and the surface of web 60 may be perforated, non-solid and/or interlacing. Web 60 maintains first member 54 and second member 56 in substantially parallel alignment in a substantially unstressed condition of bracket 28. As a stress and/or force such as, for example, flexion or extension is applied to the vertebral rod system and bracket 28, web 60 provides flexibility to bracket 28 facilitating multi axial movement of vertebral rod 20. Web 60 facilitates such multi axial movement by allowing members 54, 56 to flexibly converge to engagement and/or elastic deformation, flexibly diverge apart and rotate relatively. Second member 56 can rotate an angle α relative to first member 54. Second member 56 can rotate angle α when stress is applied to vertebral rod 20, such as, for example, a flexion or extension force being applied to bracket 28. It is contemplated that second member 56 can rotate angle α in a range of approximately −30° to 30°. It is contemplated that first member 54 and second member 56 may be disposed in alternative orientations in a substantially unstressed condition of bracket 28, such as, for example, non-parallel, converging, diverging, offset and/or staggered.

Second member 56 may also, or alternatively, rotate an angle β relative to first member 54. Second member 56 can rotate angle β when stress is applied to vertebral rod 20 such as, for example, a torsional force being applied to bracket 28. It is contemplated that second member 56 can rotate angle β in a range of approximately −20° to 20°.

Web 60 is configured to facilitate rotation of second member 56 through angle α and/or angle β, and return to an unstressed position, (for example, see FIG. 2) such that second member 56 can return to substantially parallel alignment with first member 54. The range of angles α and β can be regulated and/or selected based on the configuration and material of first member 54, second member 56 and web 54. It is envisioned that the flexibility of the vertebral rod system can be varied by varying the thickness, the length along longitudinal axis a, the width and/or the height of web 60.

Second member 56 extends to a second portion of bracket 28 such as, for example, a flange 62. Flange 62 has a thickness t and defines an opening 64 configured to receive vertebral rod 20. Opening 64 defines a longitudinal axis that is coaxial with longitudinal axis a, and supports vertebral rod 20. Vertebral rod 20 is slidably supported with opening 64 for multi axial movement relative to pedicle screw assembly 22. Opening 64 is oriented transverse to longitudinal axis b in an unstressed condition of the vertebral rod system and bracket 28.

Figure 2:
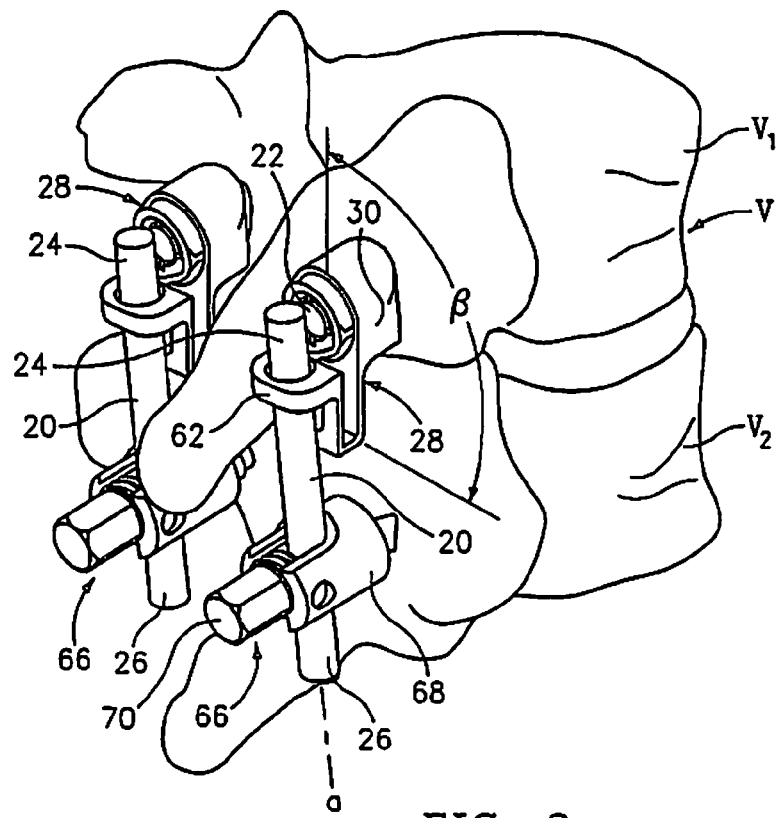
FIG. 2 is a perspective view of the vertebral rod system shown in FIG. 1 attached to vertebrae.

The vertebral rod system can include a second bracket 28 and a second pedicle screw assembly 22 for fastening an upper section 24 of a second vertebral rod 20 vertebrae V, as shown in FIG. 2 and discussed below. Pedicle screw assembly 22 does not directly engage vertebral rod 20 and is supported within opening 64. Pedicle screw assembly 22 directly engages collar 30 for fastening the vertebral rod system with vertebrae V. The vertebral rod system also includes pedicle screw assemblies 66 that directly engage lower section 26 of vertebral rods 20 for fastening the vertebral rod system with vertebrae V.

It is contemplated that the vertebral rod system may include a set or kit having one of each of vertebral rod 20, bracket 28 and pedicle screw assembly 22, or alternatively, the vertebral rod system can include a set or kit having a plurality of vertebral rods 20, brackets 28 and pedicle screw assemblies 22 that may be employed for a vertebral rod system spanning multiple levels and/or use with a long spinal construct.

Figure 3:
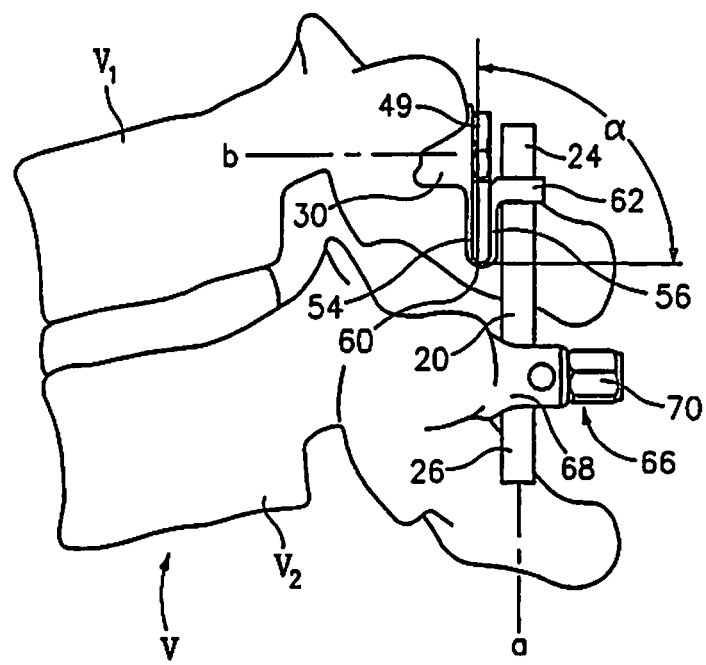
FIG. 3 is a side view of the vertebral rod system and vertebrae shown in FIG. 2.
Figure 4:
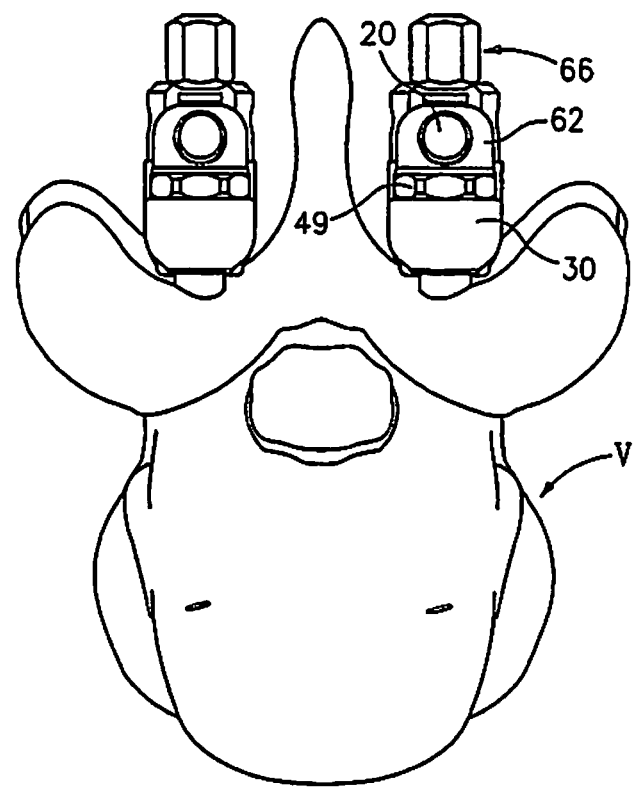
FIG. 4 is a plan view of the vertebral rod system and vertebrae shown in FIG. 2.

In assembly, operation and use, the vertebral rod system is employed with a surgical procedure for treatment of a spinal disorder affecting a section of a spine of a patient, as discussed herein. The vertebral rod system may also be employed with other surgical procedures. In particular, the vertebral rod system is employed with a surgical procedure for treatment of a condition or injury of an affected section of the spine including vertebrae V, as shown in FIGS. 2-4. It is contemplated that the vertebral rod system is attached to vertebrae V for dynamic stabilization of the affected section of the spine to facilitate healing and therapeutic treatment, while providing flexion, extension and torsion capability.

In use, to treat the affected section of the spine, a medical practitioner obtains access to a surgical site including vertebra V in any appropriate manner, such as through incision and retraction of tissues. It is envisioned that the vertebral rod system may be used in any existing surgical method or technique including open surgery, mini-open surgery, minimally invasive surgery and percutaneous surgical implantation, whereby the vertebrae V is accessed through a micro-incision, or sleeve that provides a protected passageway to the area. Once access to the surgical site is obtained, the particular surgical procedure is performed for treating the spinal disorder. The vertebral rod system is then employed to augment the surgical treatment. The vertebral rod system can be delivered or implanted as a pre-assembled device or can be assembled in situ. The vertebral rod system may be completely or partially revised, removed or replaced, for example, replacing vertebral rod 20 and using the in-place fastening elements.

Fastening elements, such as, for example, pedicle screw assemblies 22 are configured to attach collars 30 and upper sections 24 to vertebra $V_1$. Fastening elements, such as, for example, pedicle screw assemblies 66 are configured to attach lower sections 26 of vertebral rods 20 to adjacent vertebra $V_2$. Pilot holes are made in vertebrae $V_1$, $V_2$ for receiving pedicle screw assemblies 22, 66. Pedicle screw assemblies 22, 66 include threaded bone engaging portions that are inserted or otherwise connected to vertebrae $V_1$, $V_2$, according to the particular requirements of the surgical treatment. Locking nut 49 fixes pedicle screw assembly 22 with collar 30, as discussed. Pedicle screw assembly 66 has a head 68 with a bore, or through opening and a set screw 70, which is torqued on to section 26 to attach vertebral rod 20 in place with vertebrae V.

As shown in FIG. 2, the vertebral rod system includes two axially aligned and spaced apart vertebral rods 20, with sections 24 extending through flanges 62 and sections 26 extending through the bores of heads 68. Upon fixation of the vertebral rod system with vertebrae V, brackets 28 are configured to provide flexibility in response to movement of vertebral rods 20 during flexion, extension and torsion of the spine. For example, vertebral rod 20, as shown in FIGS. 2-4, is in an unloaded state such that there is no appreciable tensile, compressive or torsional loads on vertebrae $V_1$, $V_2$. In flexion, extension and/or torsion of vertebrae V caused by corresponding movement of the patient, stress and/or forces are applied to the vertebral rod system and brackets 28 react with flexibility to provide multiple axial movement of vertebral rod 20 to a plurality of orientation(s). It is contemplated that bracket 28 may provide resistance, which may be increasing, decreasing, gradual, dynamic and/or static during flexion, extension and/or torsion.

It is envisioned that the vertebral rod system including the alternate embodiments described may be employed in a configuration for vertebral stabilization over a plurality of intervertebral levels, including treated and untreated vertebral and intervertebral levels.

The vertebral rod system can be used with various bone screws, pedicle screws or multi-axial screws used in spinal surgery. It is contemplated that the vertebral rod system may be used with pedicle screws coated with an osteoconductive material such as hydroxyapatite and/or osteoinductive agent such as a bone morphogenic protein for enhanced bony fixation to facilitate motion of the treated spinal area. The components of the vertebral rod system can be made of radiolucent materials such as polymers. Radiomarkers may be included for identification under x-ray, fluoroscopy, CT or other imaging techniques. Metallic or ceramic radiomarkers, such as tantalum beads, tantalum pins, titanium pins, titanium endcaps and platinum wires can be used, such as being disposed at the end portions of vertebral rod 20 and/or along the length thereof.

In an alternate embodiment, the vertebral rod system includes a long spinal construct, a vertebral connector and a pedicle screw construct, similar to those described above, whereby the connector provides a flexible connection of the spinal construct to the pedicle screw construct at a superior level of the spinal construct. The connector integrates a flexible linking portion including an elastic element between the spinal construct and the pedicle screw construct. The elastic element is a polymer with mechanical properties suitable for a vertebral rod application.

In another alternate embodiment, bracket 28 described above is a flexible junction device, which allows at least some degree of rod motion in multiple directions. It is contemplated that the degree of rod motion can be controlled by the geometry and material properties of bracket 28, which include varying the thickness, length, width and/or height of the components thereof. It is further contemplated that bracket 28 absorbs stress to avoid screw overload from pedicle screw assembly 22. It is envisioned that bracket 28 has a three dimensional "C" shape. It is further envisioned that bracket 28 can be made with a controlled variation in size to provide the accommodation of the anatomical variations of a patient's spine.

Figure 5:
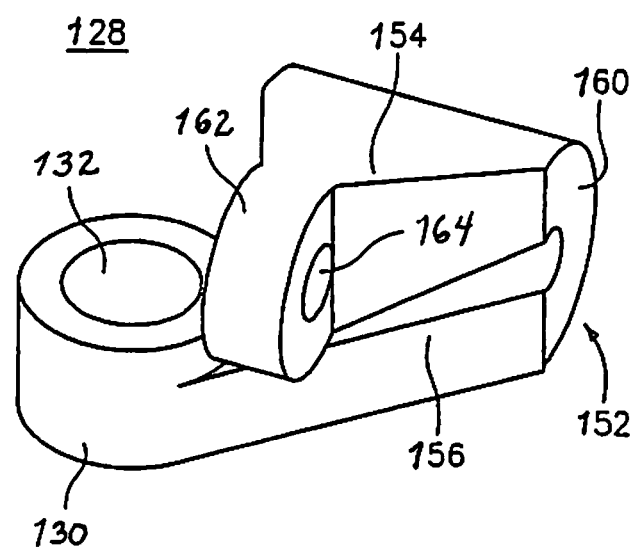
FIG. 5 is a perspective view of an alternate embodiment of a vertebral rod connector.

Referring to FIG. 5, in an alternate embodiment of the vertebral rod connector, similar to that described with regard to FIGS. 1-4, a vertebral rod bracket 128 is shown. Vertebral rod bracket 128 includes a first portion such as, for example, a collar 130 that defines a cavity 132 configured to receive a pedicle screw assembly for support thereof.

A flexible linking portion, such as, for example, a bifurcated member 152 includes a first member 154 and a second member 156 disposed in substantially parallel alignment. First member 154 is connected with second member 156 via an arcuate web 160. Web 160 allows members 154, 156 to flexibly converge to engagement and/or elastic deformation, flexibly diverge apart and rotate relatively. Second member 156 can rotate relative to first member 154 via web 160, similar to that discussed with regard to FIGS. 1-4.

Second member 156 extends to a second portion, such as, for example, a flange 162 configured to support a vertebral rod within an opening 164. In flexion, extension and/or torsion of vertebrae caused by corresponding movement of the patient, stress and/or forces are applied to the vertebral rod system and bracket 128 reacts with flexibility to provide multiple axial movement of a vertebral rod to a plurality of orientations.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A vertebral rod connector comprising:
    a first portion configured to engage a fastener construct and define a first longitudinal axis; the fastener construct configured to secure the first portion to a vertebra
    a second portion including continuous top and bottom surfaces extending between opposite side surfaces that are each continuous with the top and bottom surfaces, the second portion comprising an uninterrupted inner surface that defines an enclosed opening positioned between the top and bottom surfaces and configured for disposal of a vertebral rod, the opening extending along a second longitudinal axis disposed transverse to the first longitudinal axis, wherein the opening is configured to receive a vertebral rod such that the inner surface prevents the rod from moving along the first longitudinal axis in opposite first and second directions while allowing the rod to be movable along the second longitudinal axis; and
    a flexible linking portion disposed for connecting the first portion with the second portion, the linking portion having a bifurcated configuration oriented transverse to the first longitudinal axis.

2. A vertebral rod connector according to claim 1, wherein the first portion includes an elongated collar comprising an uninterrupted inner surface that defines an enclosed opening having a circular cross section configured to receive the fastener construct.

3. A vertebral rod connector according to claim 1, further comprising the fastener construct, wherein the fastener construct includes a pedicle screw assembly and the first portion includes an enclosed opening that extends through opposite to and bottom surfaces of the first portion that extend parallel to the second longitudinal axis, the pedicle screw assembly being disposed in the enclosed opening in the first portion.

4. A vertebral rod connector according to claim 1, wherein the first portion includes a tubular insert configured for disposal within the cavity, the insert being configured to receive the fastener construct, the insert comprising an unthreaded distal portion and a threaded proximal portion extending from a proximal end of the distal portion, the proximal portion having a uniform first diameter, the distal portion having a maximum diameter that is greater than the first diameter, the proximal portion comprising a wall that includes a plurality of equidistantly spaced apart openings configured to provide flexibility to the wall.

5. A vertebral rod connector according to claim 1, wherein the bifurcated configuration includes a first member integrally formed with the first portion and a second member integrally formed with the second portion.

6. A vertebral rod connector according to claim 5, wherein the first member and the second member are disposed in substantially parallel alignment, the first member being disposed in a first plane and the second member being disposed in a second plane, the first and second planes each extending parallel to the second longitudinal axis, the first plane being offset relative to the second plane along the first longitudinal axis.

7. A vertebral rod connector according to claim 5, wherein the first member includes an opening extending parallel to the first longitudinal axis.

8. A vertebral rod connector according to claim 7, wherein the second member includes an opening that is coaxial with the opening in the first member.

9. A vertebral rod connector according to claim 5, wherein the first member is connected with the second via an arcuate web such that the first portion is permanently connected to the second portion and the second member is rotatable relative to the first member in a range of −30 degrees to 30 degrees.

10. A vertebral rod bracket comprising:
    an elongated collar defining a cavity configured to receive a fastener construct and defining a longitudinal axis; the fastener construct configured to secure the first portion to a vertebra
    a flexible bifurcated extension disposed in a transverse orientation relative to the longitudinal axis and including a first member extending from the elongated collar and a second member; and
    a flange extending from the second member comprising continuous top and bottom surfaces extending between opposite side surfaces that are continuous with the top and bottom surfaces, the flange comprising an uninterrupted inner surface defining one enclosed opening positioned between the top and bottom surfaces and orientated transverse to the longitudinal axis, the opening being configured to receive a vertebral rod such that the inner surface of the flange prevents the rod from moving along the longitudinal axis in opposite first and second directions while allowing the rod to slide along an axis that extends transverse to the longitudinal axis.

11. A vertebral rod bracket according to claim 10, further comprising the fastener construct, wherein the fastener construct includes a pedicle screw assembly and the cavity defines an enclosed opening that extends through opposite to and bottom surfaces of the collar that extend transverse to the longitudinal axis, the pedicle screw assembly being disposed in the enclosed opening in the collar.

12. A vertebral rod bracket according to claim 10, wherein the collar includes a tubular insert configured for disposal within the cavity, the insert being configured to receive the fastener construct, the insert comprising an unthreaded distal portion and a threaded proximal portion extending from a proximal end of the distal portion, the proximal portion having a uniform first diameter, the distal portion having a maximum diameter that is greater than the first diameter, the proximal portion comprising a wall that includes a plurality of equidistantly spaced apart openings configured to provide flexibility to the wall.

13. A vertebral rod bracket according to claim 10, wherein the first member is disposed in a first plane and the second member is disposed in a second plane, the first and second planes each extending parallel to the opening in the flange, the first plane being offset relative to the second plane along the longitudinal axis.

14. A vertebral rod bracket according to claim 10, wherein the first member includes an elongated opening that is spaced apart from the cavity and extends parallel to the longitudinal axis.

15. A vertebral rod bracket according to claim 14, wherein the second member includes an elongated opening that extends parallel to the longitudinal axis and is coaxial with the elongated opening in the first member.

16. A vertebral rod bracket according to claim 10, wherein the first member is integrally formed with the collar, the second member is integrally formed with the flange and the first member is connected with the second member via an arcuate web.

\* \* \* \* \*